(12) United States Patent
Wieters et al.

(10) Patent No.: US 10,365,470 B2
(45) Date of Patent: Jul. 30, 2019

(54) ENDOSCOPE HAVING A LATERAL DIRECTION OF VIEW

(71) Applicant: OLYMPUS WINTER & IBE GMBH, Hamburg (DE)

(72) Inventors: Martin Wieters, Barsbuettel (DE); Alrun Thuemen, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 609 days.

(21) Appl. No.: 14/987,853

(22) Filed: Jan. 5, 2016

(65) Prior Publication Data
US 2016/0124211 A1 May 5, 2016

Related U.S. Application Data

(63) Continuation of application No. PCT/EP2014/001683, filed on Jun. 20, 2014.

(30) Foreign Application Priority Data

Jul. 5, 2013 (DE) .................. 10 2013 213 232

(51) Int. Cl.
| | |
|---|---|
| *G02B 23/00* | (2006.01) |
| *A61B 1/00* | (2006.01) |
| *G02B 23/24* | (2006.01) |

(52) U.S. Cl.
CPC ........ *G02B 23/2476* (2013.01); *A61B 1/0011* (2013.01); *A61B 1/00071* (2013.01);
(Continued)

(58) Field of Classification Search
CPC . G02B 7/00; G02B 7/003; G02B 7/02; G02B 7/021; G02B 7/022; G02B 7/023;
(Continued)

(56) References Cited

U.S. PATENT DOCUMENTS

| | | | | |
|---|---|---|---|---|
| 5,383,791 A | * | 1/1995 | Hirakui | .............. H01R 13/5224 439/135 |
| 5,486,155 A | | 1/1996 | Muller et al. | |

(Continued)

FOREIGN PATENT DOCUMENTS

| | | |
|---|---|---|
| CN | 101732025 A | 6/2010 |
| DE | 102011078968 A1 | 1/2013 |

(Continued)

OTHER PUBLICATIONS

Chinese Office Action dated Jun. 30, 2017 in Chinese Patent Application No. 201480038589.2.

(Continued)

*Primary Examiner* — Thong Q Nguyen

(74) *Attorney, Agent, or Firm* — Scully, Scott, Murphy & Presser, P.C.

(57) ABSTRACT

An endoscope including: an endoscope shaft having an outer tube and an inner tube rotatable relative to each other, the outer tube radially surrounding the inner tube; a first optical assembly disposed in a distal region of the endoscope shaft and being accommodated in and/or operated by the outer tube; a second optical assembly disposed in the distal region and being accommodated in the inner tube; an axial bearing arranged between the outer tube and the inner tube in a proximal region of the endoscope shaft wherein the axial bearing includes an outer ring associated with the outer tube and an inner ring associated with the inner tube; and a fixing device for the axial bearing, the fixing device including a first elastomer body provided for the outer ring of the axial bearing and/or a second elastomer body provided for the inner ring of the axial bearing.

14 Claims, 3 Drawing Sheets

(52) U.S. Cl.
CPC ...... *A61B 1/00172* (2013.01); *G02B 23/2423* (2013.01); *A61B 1/00179* (2013.01)

(58) Field of Classification Search
CPC . G02B 7/026; G02B 7/20; G02B 7/24; G02B 23/16; G02B 23/24; G02B 23/2423; G02B 23/2453; G02B 23/2476; A61B 1/00006; A61B 1/00096; A61B 1/0057; A61B 1/0058; A61B 1/04; A61B 1/05; A61B 1/051
See application file for complete search history.

(56) References Cited

U.S. PATENT DOCUMENTS

| | | | |
|---|---|---|---|
| 2002/0133077 A1 | 9/2002 | Edwardsen et al. | |
| 2007/0112254 A1* | 5/2007 | Weigel | A61B 1/05 600/137 |
| 2011/0245827 A1* | 10/2011 | Okada | A61B 17/29 606/41 |
| 2012/0190921 A1* | 7/2012 | Yadlowsky | A61B 1/00172 600/106 |
| 2012/0245569 A1* | 9/2012 | Papac | A61F 9/00763 606/1 |
| 2014/0128679 A1 | 5/2014 | Wieters | |
| 2016/0010401 A1* | 1/2016 | Fulda | E21B 10/02 175/58 |

FOREIGN PATENT DOCUMENTS

| | | |
|---|---|---|
| EP | 1787570 A1 | 5/2007 |
| JP | H03-172617 A | 7/1991 |
| WO | 2013/007356 A1 | 1/2013 |

OTHER PUBLICATIONS

International Search Report dated Oct. 6, 2014 issued in PCT/EP2014/001683.

Japanese Office Action dated Apr. 4, 2017 in Japanese Patent Application No. 2016-522312.

* cited by examiner

# ENDOSCOPE HAVING A LATERAL DIRECTION OF VIEW

CROSS-REFERENCE TO RELATED APPLICATION

The present application is a continuation of PCT/EP2014/001683 filed on Jun. 20, 2014, which is based upon and claims the benefit to DE 10 2013 213 232.8 filed on Jul. 5, 2013, the entire contents of each of which are incorporated herein by reference.

BACKGROUND

Field

The present application relates to an endoscope, such as an endoscope having a lateral direction of view, comprising an endoscope shaft, which has an outer tube and an inner tube, which is surrounded by the outer tube, wherein the outer tube is configured to accommodate and/or to operate a first optical assembly in the distal region of the endoscope shaft, and wherein the inner tube is configured to accommodate a second optical assembly in the distal region of the endoscope shaft, wherein the inner tube and the outer tube are mounted in such a way that the inner tube and the outer tube can be rotated in relation to each other, and wherein an axial bearing is arranged between the outer tube and the inner tube in the proximal region of the endoscope shaft, and wherein the axial bearing has an outer ring, which is associated with the outer tube, and an inner ring, which is associated with the inner tube.

Within the framework of the present disclosure, the term endoscope includes video endoscopes, i.e. endoscopes in connection with at least one image sensor, which can be configured to record a video recording, regardless of whether the image sensor is arranged distally in the endoscope shaft, proximally in a handle or externally in a camera head, which can be placed on an eyepiece in the proximal region of the endoscope, i.e. on the side of an operator.

The term "direction of view" (DOV) relates to the sideways and backwards view deviating from the longitudinal axis of the endoscope, which is represented as the polar angle, wherein an angle of view of 0° indicates a straight-ahead view in the longitudinal direction of the endoscope shaft, while for example, an angle of view of 90° indicates a direction of view deviating from the straight-ahead view at a right angle.

Prior Art

In the case of endoscopes, such as video endoscopes with a direction of view≠0°, it is necessary that two optical assemblies can be moved relative to each other rotationally in the distal optical system. For this, a radial and axial mounting of the optical assemblies is necessary. The radial mounting restricts the relative movement of the assemblies relative to each other in the radial direction; the axial mounting restricts the relative movement in the axial direction of the endoscope. In order to avoid negatively impacting the optical quality, it is also advantageous if the axial mounting is built without play in order to not change the optical path by an axial displacement of the optical assemblies relative to each other.

In the state of the art, the axial absence of play is created by the pretensioning of the mounting with a spring, for example a spiral spring, which is located in the handle region of the endoscope.

In the case of the video endoscope according to EP 1 787 570 B1, a radially acting mounting is located in the handle. Both a radial and an axial mounting are located between the two distal optical assemblies. Both the torque, as well as the axial force are transferred via two tubes, to each of which an optical assembly is connected. The distally arranged axial mounting is hereby held axially and without play by means of the spring placed in the handle region.

Through the spring placed in the handle for state-of-the-art endoscopes for pretensioning the axial mounting, axial forces must also be transferred in addition to the torque. The structure is hereby relatively complicated and complex.

Moreover, video endoscopes with a lateral direction of view, i.e. a direction of view not equal to 0°, are known, in which a distal deflection prism of a first optical group is accommodated by an outer tube and the image sensor unit of the second optical group, such as a CCD image sensor unit, is arranged in an inner tube. The two tubes for the optical assemblies are in this case tensioned by a spring in the proximal handle region, wherein a radial mounting is provided in the distal region of the endoscope shaft between the outer tube and the inner tube. The installation of the spring is very complex. Moreover, the mounting of the inner tube and of the outer tube is very rigid since the distance between the tubes is very small. Since the optical assemblies provided for the inner tube and the outer tube also have a small, radial separation distance, it can happen that this leads to a jam in the endoscope shaft in the distal region.

FIG. 1 shows schematically an endoscope 1 known from the state of the art. The endoscope 1 has on the proximal end shown on the right a handle 3, which opens into a shaft 2. The distal end of the shaft 2 is shown on the left side in FIG. 1.

The handle 3 has a rotary swivel 4, by means of which via bar magnets 5, which are connected with an inner tube 7, the inner tube 7 can be turned with respect to an outer tube 6 in order to change the direction of view of the endoscope 1. In the handle 3, the inner tube 7 is also mounted by means of a radial bearing 8. Moreover, the handle 3 comprises a pretensioning device comprising a compression spring 9, which is pretensioned with respect to a stop 10 for the compression spring 9. The compression spring 9 ensures that the inner tube 7 in the axial direction is pushed or respectively pretensioned towards the distal end 11 of the shaft 2.

On the distal end 11, the shaft 2 has a window 12, which looks sideways. An optical assembly 13 with lenses and prisms, with which the light entering through the window 12 is directed in a direction parallel to the longitudinal axis of the shaft 2, is located behind the window 12. The optical assembly 13 is held by a holder 14, which is connected with the outer tube 6. The window 12 is also part of the optical assembly 13.

A second optical assembly 16, which in this case ends in an image sensor unit 19, connects proximally to the first optical assembly 13. The second optical assembly 16 is mounted in a holder 17, which is connected with the inner tube 7 such that it performs rotations or displacements of the inner tube 7. The inner tube 7 is mounted radially with respect to the outer tube 6 in the region of the distal end 11 of the shaft 2 by means of a radial mounting 18.

The distal front surface of the holder 17 of the second optical assembly 16 and the proximal front surface of the holder 14 of the first optical assembly 13 are arranged opposite each other and form an axial bearing 15. Through the pretensioning of the inner tube 7 in the axial direction by the compression spring 9 in the handle 3, the axial bearing 15 is closed, i.e. the distal-side front surface of the holder 17 is pushed against the proximal-side front surface of the holder 14. The axial position of the second optical assembly 16 with respect to the first optical assembly 13 is thus set and an optimal optical quality is achieved.

Since the axially acting pretensioning force is conveyed via the longitudinally extending inner tube 7, any tilting, twisting or displacement of the inner tube 7 in the outer tube 6 leads to the axially acting pretensioning force not being optimally transferred to the axial bearing 15. This can lead to an impairment of the optical quality.

SUMMARY

Based on this state of the art, an object is thus to provide an endoscope, such as those having a lateral direction of view, in which a jam is prevented in the distal region of the endoscope shaft and wherein production deviations of the assemblies for an endoscope are compensated for in a simple manner.

Such object is solved by an endoscope, such as an endoscope having a lateral direction of view, comprising an endoscope shaft, which has an outer tube and an inner tube, which is surrounded by the outer tube, wherein the outer tube can be configured to accommodate and/or to operate a first optical assembly in the distal region of the endoscope shaft, and wherein the inner tube can be configured to accommodate a second optical assembly in the distal region of the endoscope shaft, wherein the inner tube and the outer tube are mounted in such a way that the inner tube and the outer tube can be rotated in relation to each other, and wherein an axial bearing is arranged between the outer tube and the inner tube in the proximal region of the endoscope shaft, and wherein the axial bearing has an outer ring, which is associated with the outer tube, and an inner ring, which is associated with the inner tube, which is further developed in that a fixing device for the axial bearing has an elastomer body provided for the outer ring of the axial bearing and/or an elastomer body provided for the inner ring of the axial bearing.

In the case of the first optical assembly for the endoscope, the first assembly comprises optical windows, prisms and/or lenses. In the case of the design as an endoscope with a lateral direction of view, the first optical assembly hereby has corresponding sideways-looking optical windows. In the case of the second optical assembly, the same comprises lenses and/or a straight-ahead-looking image sensor, wherein the image sensor and/or the second optical assembly is or are aligned in the direction of the longitudinal axis of the endoscope shaft.

Due to the fact that respectively one elastomer body can be provided in the proximal region of the endoscope shaft for the outer ring of the axial bearing provided in the proximal end region of the endoscope shaft and/or for the inner ring of the axial bearing, it is possible to compensate for geometrical deviations between the first optical assembly for the outer tube and of the second optical assembly for the inner tube when using a ball bearing as an axial bearing between the inner tube and the outer tube. In the distal end region of the endoscope shaft, a radial slide bearing can be provided as the radial bearing between the inner tube and the outer tube.

Moreover, a jam-free tipping of the distal-side tube ends of the endoscope shaft between 10° to 15°, in relation to the radial longitudinal axis of the endoscope shaft or respectively the outer and the inner tube, as a result of the arrangement of the elastomer bodies between the inner tube and the outer tube, is possible, whereby the handling of an endoscope is correspondingly improved.

Through the use of elastomer bodies, which can abut against the outer ring and the inner ring of the proximal axial bearing, the axial bearing provided in the proximal region of the endoscope shaft for the outer tube and the inner tube is fixed so that no or respectively only a very small axial displacement can occur between the optical assemblies of the outer tube and the inner tube.

Due to the fact that the elastomer bodies are made of an elastomeric material, they can be used for fixing the axial bearing in the proximal region of the endoscope shaft. A cost-effective design of the fixing device for the axial bearing can hereby take place using so-called O-rings. In the case of the use of O-rings as elastomer bodies for the outer ring of the axial bearing and for the inner ring of the axial bearing, the (ring) diameter of the O-ring for the outer ring is hereby greater than the (ring) diameter of the O-ring for the inner ring.

For this, it is provided in a further development that the elastomer body for the outer ring of the axial bearing can be configured annularly, i.e. as an O-ring or the like and/or the elastomer body for the inner ring of the axial bearing can be configured annularly, i.e. for example as an O-ring.

It is provided in an advantageous embodiment of the endoscope that the elastomer body for the outer ring of the axial bearing is made of fluoro rubber (FKM) or fluorocarbon rubber or ethylene propylene diene rubber (EPDM) or silicone and/or the elastomer body for the inner ring of the axial bearing is made of fluoro rubber (FKM) or fluorocarbon rubber or ethylene propylene diene rubber (EPDM) or silicone. Moreover, the elastomer bodies or respectively O-rings can be made of elastomers other than those named.

Furthermore, the elastomer body for the outer ring of the axial bearing can be arranged on the side of the outer ring facing the distal region of the endoscope or the elastomer body for the outer ring of the axial bearing can be arranged on the side of the outer ring facing the proximal region of the endoscope.

Furthermore, it is also provided in one embodiment of the endoscope that the elastomer body for the inner ring of the axial bearing is arranged on the side of the inner ring facing the distal region of the endoscope or the elastomer body for the inner ring of the axial bearing is arranged on the side of the inner ring facing the proximal region of the endoscope.

Still further, the elastomer body for the outer ring of the axial bearing and the elastomer body for the inner ring of the axial bearing can be arranged on the same side of the axial bearing or the elastomer body for the outer ring of the axial bearing and the elastomer body for the inner ring of the axial bearing can be arranged on different sides of the axial bearing.

Still further yet, the elastomer bodies can fix the axial bearing or respectively the ball bearing, wherein, in one embodiment, the elastomer body for the outer ring abuts against the proximal side of the axial bearing and the elastomer body for the inner ring abuts against the distal side of the axial bearing. In a further embodiment, the elastomer body for the outer ring can be arranged adjacent to the distal side of the axial bearing and the elastomer body for the inner ring can be arranged adjacent to the proximal side of the axial bearing.

Furthermore, according to a third variant, the elastomer body for the outer ring and the elastomer body for the inner ring of the axial bearing can be either arranged on the proximal side, i.e. on the side of the axial bearing pointing towards the proximal region of the endoscope, or on the side of the axial bearing pointing towards the distal side.

Moreover, in the case of an endoscope, such as an endoscope with a lateral direction of view, a receiver for the outer ring of the axial bearing and the elastomer body for the outer ring of the axial bearing can be provided on the inside of the outer tube, wherein the width of the receiver for the outer ring and the elastomer body for the outer ring can be less than or equal to the total width of the outer ring of the axial bearing and the width or respectively the height of the elastomer body for the outer ring. The receiver can be configured in a groove-shaped manner on the inside of the outer tube, wherein a flank of the receiver or respectively of the circumferential receiving groove is configured as a stop for a side or respectively for the outer ring of the axial bearing. The other side or respectively flank of the receiving groove can be in contact with the elastomer body.

Moreover, in one embodiment of the endoscope that a receiver, such as a receiving groove, for the inner ring of the axial bearing and the elastomer body for the inner ring can be provided on the outside of the inner tube, wherein the width of the receiver for the inner ring of the axial bearing and for the elastomer body for the inner ring can be less than or equal to the total width of the inner ring of the axial bearing and of the width or respectively height of the elastomer body for the inner ring. The inner ring of the axial bearing and the elastomer body for the inner ring can be arranged between the flanks of the receiver on the outside of the inner tube, wherein the width of the receiver or respectively of the receiving groove can be less than the width of the inner ring of the axial bearing and of the width (or height) of the elastomer body, such as a non-pretensioned elastomer body, for the inner ring.

Furthermore, in one embodiment of the endoscope, the inner tube can be configured in order to accommodate the second optical assembly and the first optical assembly provided on the distal end, wherein the first optical assembly is or will be subjected to a force acting in the proximal direction by means of a force transmission device, such as a magnetic fixing device or mechanical spring device. It is hereby provided that the first optical assembly provided on the outer distal end can be operable or operated using the rotatably mounted outer ring, such as under formation of a coupling device between the outer ring and the first optical assembly, in order to effectuate a radial movement of the first optical assembly or parts of it.

The axial bearing provided in the proximal end region of the endoscope shaft can be configured between the outer tube and the inner tube as a raw dial groove ball bearing or as an angular ball bearing.

Further characteristics will be evident from the description of embodiments together with the claims and the included drawings. Embodiments can fulfill individual characteristics or a combination of several characteristics.

BRIEF DESCRIPTION OF THE DRAWINGS

Without restricting the general idea of the invention, the invention is described below on the basis of exemplary embodiments with reference to the drawings, whereby reference is explicitly made to the drawings with regard to all the details, which are not described in more detail in the text. In the figures.

In the drawings, the same or similar elements and/or parts are provided with the same reference numbers in order to prevent the item from needing to be reintroduced.

DETAILED DESCRIPTION

Figure 1:
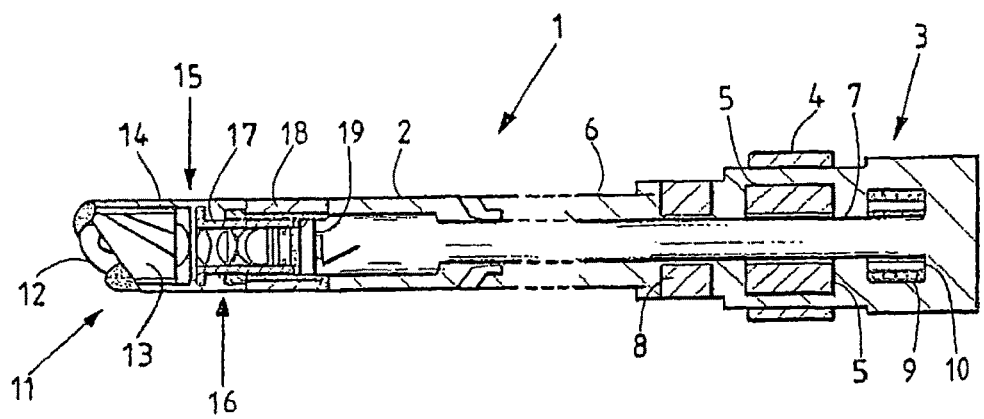
FIG. 1 is a schematic illustration of an endoscope according to the state of the art.

FIGS. 2 to 6 show schematically in cross-section embodiments for an axial bearing in the proximal region of an endoscope. This hereby concerns detailed sections on the proximal end and on the distal end of the shaft 2, which is not shown in greater detail below. For the sake of clarity, FIGS. 2 to 6 each show only the optical assemblies in detail in the distal region as well as the fixing device for the axial bearing in the proximal region. It hereby generally applies in the shown embodiments that springs or other pretensioning devices in the handle 3 of the endoscope 1 (see FIG. 1) are dispensable and can thus be omitted entirely.

The elongated shaft of the endoscope is shown shortened schematically in each of FIGS. 2 to 6. The outer tube 6 and the inner tube 7 extend from the proximal end up to the distal end of the endoscope shaft. A radial bearing 21, such as a radial slide bearing, is provided in the distal end region between the inner tube 7 and the outer tube 6, and an axial bearing 22, such as a ball bearing, is arranged in the proximal end region of the endoscope shaft between the inner tube 7 and the outer tube 6. On the left side in each of FIGS. 2 to 6, the distal end of the endoscope shaft is shown with the radial bearing 21 and, on the right side in each of the figures, the proximal end of the endoscope shaft is shown with the axial bearing 22.

Figure 2:
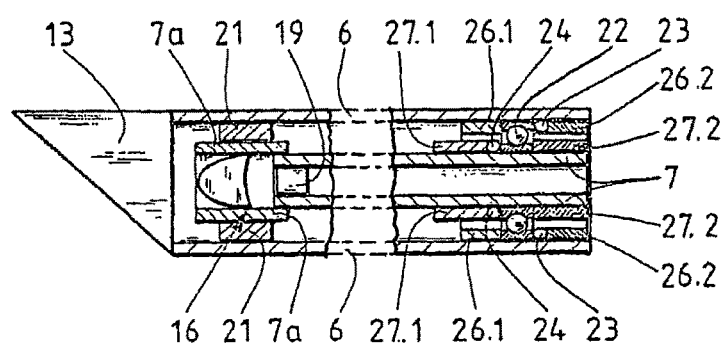
FIG. 2 is a schematic illustration in cross-section, of a representation of an axial bearing in the proximal region of the endoscope.

In the case of the embodiment shown in FIG. 2, the first optical assembly 13 provided on the distal side is arranged on the outer tube 6. The inner tube 7 is arranged inside the outer tube 6, on which the image sensor 19, such as a CCD sensor, is arranged on the distal side. Furthermore, a lens 20 is arranged in an inner tube section 7a of the tube continued on the distal side on the inner tube 7. The lens 20 and the image sensor unit 19 are part of the second optical assembly, which is connected with the inner tube 7. A radial bearing 21, which serves to guide and hold the inner tube section 7a centered, is arranged between the inner tube section 7a and the inside of the outer tube 6.

Furthermore, an axial bearing 22 is provided in the proximal end region of the endoscope shaft next to the radial bearing 21, which is arranged on the distal end region. The axial bearing 22 can be configured as a radial groove ball bearing. On the inside of the outer tube 6, stop bodies 26.1, 26.2 are arranged in the region of the axial bearing 22. The stop bodies 26.1, 26.2 can be configured as sleeves and are spaced from each other in the axial direction so that a receiver is configured between the stop bodies 26.1, 26.2, in which the outer ring of the axial bearing 22 is accommodated.

Furthermore, stop bodies 27.1, 27.2, which are spaced from each other in the axial direction, are arranged on the outside of the inner tube 7 so that the stop bodies 27.1, 27.2 form a receiver for the inner ring of the axial bearing 22.

Moreover, an O-ring 23 made of an elastomeric material is additionally arranged between one side of the outer ring of the axial bearing 22 in the receiver formed by the spaced stop bodies 26.1, 26.2 in order to fix the axial bearing 22. A further O-ring 24 made of an elastomeric material is arranged on the inside or respectively on the inner ring of the axial bearing 22 between one side of the inner ring and a stop body 27.1 or 27.2 for fixing the axial bearing 22 in the receiver formed by the spaced stop bodies 27.1, 27.2.

In the embodiment in FIG. 2, the O-ring 23 arranged on the outer ring of the axial bearing 22 is arranged on the surface of the outer ring pointing toward the proximal side, while the O-ring 24 for the inner ring is arranged on the side of the axial bearing 22 pointing toward the distal end.

Figure 3:
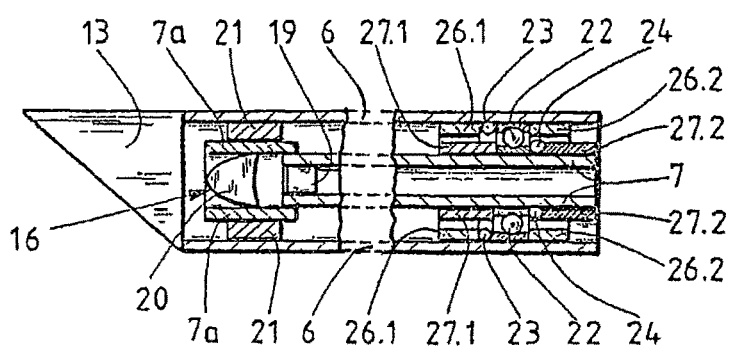
FIG. 3 is a schematic illustration in cross-section, of a further embodiment of an axial bearing in the proximal region of an endoscope.

In the embodiment in FIG. 3, the inner O-ring 24 on the inside is arranged on the proximal side on the inner ring of the axial bearing 22, while the O-ring 23 with the larger (ring) diameter abuts against the distal side of the axial bearing 22. The axial bearing 22 itself is arranged in the proximal region of the endoscope shaft.

Figure 4:
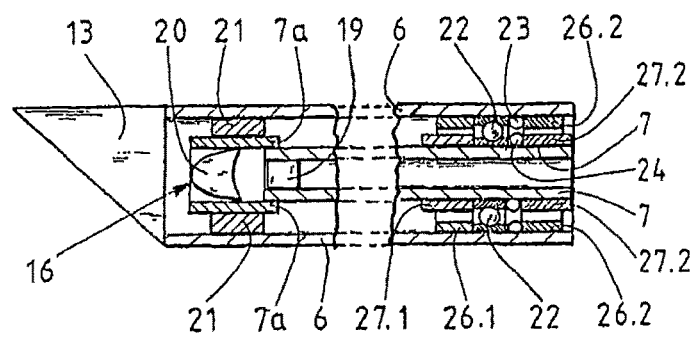
FIG. 4 is a schematic, cross-sectional illustration of an axial bearing in the proximal region of an endoscope.
Figure 5:
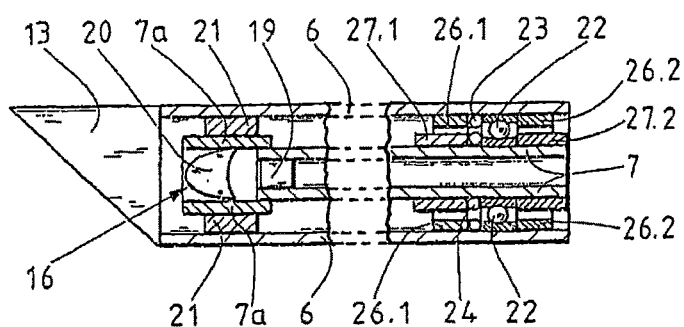
FIG. 5 is a schematic illustration of a further embodiment for a proximal axial bearing.

In the embodiment in FIG. 4, both the O-ring 23 as well as the O-ring 24 are arranged on the side of the proximal axial bearing 22 pointing toward the proximal side, while, in the embodiment in FIG. 5, the O-rings 23 abut on the distal side against the outer ring or respectively the inner ring of the axial bearing 22.

Figure 6:
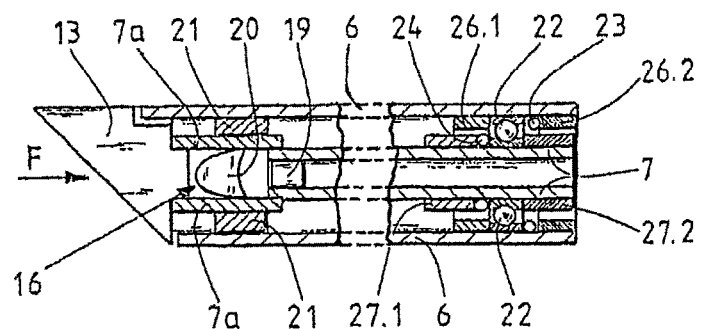
FIG. 6 is a further illustration of an axial bearing in the proximal region of an endoscope.

In the embodiment shown in FIG. 6, the first optical assembly 13 is accommodated by the inner tube section 7a on the distal side, wherein the optical assembly 13 is hereby guided radially by the distal-side receiver on the inner tube section 7a. For this, for example using a mechanical spring or a magnet or the like, a force F is exerted on the first optical assembly 13, which acts on the distal assembly 13 in the proximal direction. In order to twist the first optical assembly 13 with respect to the image sensor unit 19, the tube 6 with the optical assembly is rotatable, for example using a coupling element, on the distal side on the end of the outer tube 6.

Figure 7:
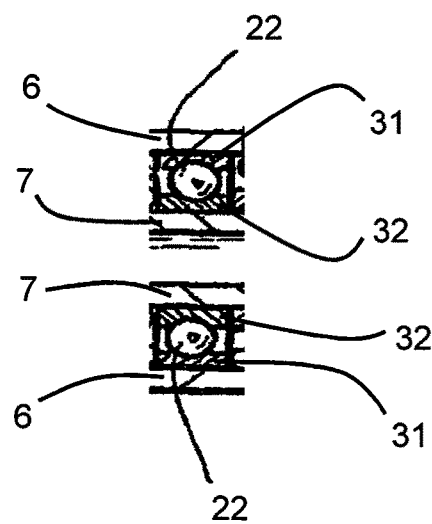
FIG. 7 illustrates an enlargement of the axial bearing of FIG. 6.

In the disclosed embodiments, the inner ring 32 and/or the outer ring 31 of the axial bearing 22 provided in the proximal end region or of the bearing in the case of a tipping load through deformation of one or more of the existing O-rings can follow the tipping movement so that a jamming of the bearing is avoided and the smooth twistability is retained (see FIG. 7).

All named characteristics, including those taken from the drawings alone, and individual characteristics, which are disclosed in combination with other characteristics, are considered alone and in combination as important. Embodiments can be realized by individual characteristics, or a combination of several characteristics.

REFERENCE LIST

1 Endoscope
2 Shaft
3 Handle
4 Rotary swivel
5 Bar magnet
6 Outer tube
7 Inner tube
7a Inner tube section
8 Radial bearing
9 Compression spring
10 Stop for compression spring
11 Distal end
12 Window
13 Optical assembly with lenses and prisms
14 Holder of the optical assembly
15 Axial bearing
16 Optical assembly
17 Holder of the optical assembly
18 Radial bearing
19 Image sensor unit
20 Lens
21 Radial bearing
22 Axial bearing
23 O-ring
24 O-ring
26.1, 26.2 Stop body
27.1, 27.2 Stop body

What is claimed is:

1. An endoscope comprising:
an endoscope shaft, which has an outer tube and an inner tube rotatable relative to each other, the outer tube radially surrounding the inner tube;
a first optical assembly disposed in a distal region of the endoscope shaft, the first optical assembly being one or more of accommodated in the outer tube and operated by the outer tube;
a second optical assembly disposed in the distal region of the endoscope shaft, the second optical assembly being accommodated in the inner tube;
an axial bearing arranged between the outer tube and the inner tube in a proximal region of the endoscope shaft wherein the axial bearing includes an outer ring associated with the outer tube and an inner ring associated with the inner tube, the axial bearing being configured to restrict relative movement of the first and second optical assemblies in an axial direction of the endoscope shaft;
a radial bearing arranged between the inner tube and the outer tube in the distal region of the endoscope shaft, the radial bearing being configured to restrict relative movement of the first and second optical assemblies relative to each other in a radial direction of the endoscope shaft; and
a fixing device for the axial bearing, the fixing device including a first elastomer body provided for the outer ring of the axial bearing and a second elastomer body provided for the inner ring of the axial bearing.

2. The endoscope according to claim 1, wherein one or more of the first elastomer body and the second elastomer body are configured annularly.

3. The endoscope according to claim 1, wherein one or more of the first elastomer body and the second elastomer body are formed from a material selected from a group consisting of fluoro rubber, fluorocarbon rubber, ethylene propylene diene rubber (EPDM) and silicone.

4. The endoscope according to claim 1, wherein the first elastomer body is arranged on one or more of a distal side of the outer ring and a proximal side of the outer ring.

5. The endoscope according to claim 1, wherein the second elastomer body is arranged on one or more of a distal side of the inner ring and a proximal side of the inner ring.

6. The endoscope according to claim 1, wherein the first elastomer body and the second elastomer body are either each arranged on a same side of the axial bearing or on different sides of the axial bearing.

7. The endoscope according to claim 1, further comprising a receiver for the outer ring of the axial bearing, wherein the first elastomer body is provided on an inside of the outer tube.

8. The endoscope according to claim 7, wherein a width of the receiver is less than or equal to a combined width of the outer ring of the axial bearing and a width of the first elastomer body.

9. The endoscope according to claim 1, further comprising a receiver for the inner ring of the axial bearing, wherein the second elastomer body is provided on an outside of the inner tube.

10. The endoscope according to claim 9, wherein a width of the receiver is less than or equal to a combined width of the inner ring of the axial bearing and a width of the second elastomer body.

11. The endoscope according to claim 1, wherein the inner tube accommodates the second optical assembly and the first optical assembly, wherein the first optical assembly is subjected to a force acting in a proximal direction by means of a power transmission device.

12. The endoscope according to claim 11, wherein the power transmission device is a magnetic fixing device.

13. The endoscope according to claim 1, wherein the axial bearing is configured as one of a radial groove ball bearing and as an angular ball bearing.

14. The endoscope according to claim 1, wherein the first optical assembly is configured to have a lateral direction of view.

* * * * *